(12) United States Patent
Zilbershlag

(10) Patent No.: US 10,561,775 B2
(45) Date of Patent: Feb. 18, 2020

(54) ALERTING A PATIENT

(71) Applicant: Leviticus Cardio Ltd., Petach Tikva (IL)

(72) Inventor: Michael Zilbershlag, Givat Shmuel (IL)

(73) Assignee: Leviticus Cardio Ltd., Petach Tikva (IL)

( * ) Notice: Subject to any disclaimer, the term of this patent is extended or adjusted under 35 U.S.C. 154(b) by 0 days.

(21) Appl. No.: 16/028,877

(22) Filed: Jul. 6, 2018

(65) Prior Publication Data

US 2018/0339093 A1 Nov. 29, 2018

Related U.S. Application Data

(63) Continuation of application No. 15/713,066, filed on Sep. 22, 2017, which is a continuation-in-part of (Continued)

(51) Int. Cl.
*A61M 1/12* (2006.01)
*H01M 2/02* (2006.01)
(Continued)

(52) U.S. Cl.
CPC .............. *A61M 1/127* (2013.01); *A61N 1/378* (2013.01); *H01M 2/0207* (2013.01); *H01M 2/06* (2013.01); *H01M 2/34* (2013.01); *H01M 10/4207* (2013.01); *H01M 10/4257* (2013.01); *H01M 10/441* (2013.01); *H01M 10/482* (2013.01);
(Continued)

(58) Field of Classification Search
CPC .......... A61M 1/127; A61M 2205/3507; A61M 2205/8206; A61M 1/12; A61N 1/378; H01M 2/0207; H01M 2/06; H01M 2/34; H01M 10/4207; H01M 10/4257; H01M 10/441; H01M 10/482; H01M 10/488; H01M 10/052; H01M 2010/4271;
(Continued)

(56) References Cited

U.S. PATENT DOCUMENTS

| | | |
|---|---|---|
| 4,143,661 A | 3/1979 | LaForge et al. |
| 4,665,896 A | 5/1987 | LaForge et al. |

(Continued)

FOREIGN PATENT DOCUMENTS

| | | |
|---|---|---|
| WO | 2007003351 A1 | 1/2007 |
| WO | 2013085996 A1 | 6/2013 |

OTHER PUBLICATIONS

Dermott, J. & Bond, J., "Safety Considerations for Lithium-Ion Flight Batteries," Power Sources Conference, Orlando, Jun. 2014, 4 pages.

(Continued)

*Primary Examiner* — Robert L Deberadinis
(74) *Attorney, Agent, or Firm* — Brown Rudnick LLP

(57) ABSTRACT

A system for alerting a patient includes a ventricular assist device (VAD), a battery, and an alarm system. All of these components of the system are configured to be implanted within the patient. The implanted alarm system is configured to provide an alert to and from within the patient based on a condition. The alert can be a vibration or an electrical shock, and the condition can be the implanted battery being below a threshold, a failure of the implanted battery, an error of the implanted battery, or an error of the implanted VAD.

7 Claims, 15 Drawing Sheets

Related U.S. Application Data application No. 14/535,528, filed on Nov. 7, 2014, now Pat. No. 9,793,579.

(60) Provisional application No. 61/901,751, filed on Nov. 8, 2013.

(51) Int. Cl.

| | | |
|---|---|---|
| *H01M 2/06* | (2006.01) | |
| *A61N 1/378* | (2006.01) | |
| *H01M 2/34* | (2006.01) | |
| *H01M 10/42* | (2006.01) | |
| *H01M 10/44* | (2006.01) | |
| *H01M 10/48* | (2006.01) | |
| H01M 10/052 | (2010.01) | |

(52) U.S. Cl.
CPC .. *H01M 10/488* (2013.01); *A61M 2205/3507* (2013.01); *A61M 2205/8206* (2013.01); *H01M 10/052* (2013.01); *H01M 2010/4271* (2013.01); *H01M 2200/00* (2013.01); *Y10T 307/625* (2015.04)

(58) Field of Classification Search
CPC .... H01M 2200/22; H01M 2/02; H01M 10/42; H01M 10/44; H01M 10/48; Y10T 307/625
See application file for complete search history.

(56) References Cited

U.S. PATENT DOCUMENTS

| | | | |
|---|---|---|---|
| 4,906,229 A | 3/1990 | Wampler | |
| 4,957,504 A | 9/1990 | Chardack | |
| 5,089,017 A | 2/1992 | Young et al. | |
| 5,095,903 A | 3/1992 | DeBellis | |
| 5,507,629 A | 4/1996 | Jarvik | |
| 5,749,855 A | 5/1998 | Reitan | |
| 5,991,665 A | 11/1999 | Wang et al. | |
| 6,070,103 A | 5/2000 | Ogden | |
| 6,129,704 A | 10/2000 | Forman et al. | |
| 6,135,729 A | 10/2000 | Aber | |
| 6,280,377 B1 | 8/2001 | Talpade | |
| 6,421,889 B1 | 7/2002 | Chien | |
| 6,527,699 B1 | 3/2003 | Goldowsky | |
| 6,531,847 B1 | 3/2003 | Tsukamoto et al. | |
| 6,761,681 B2 | 7/2004 | Schmid et al. | |
| 6,772,011 B2 | 8/2004 | Dolgin | |
| 6,891,353 B2 | 5/2005 | Tsukamoto et al. | |
| 7,433,794 B1 | 10/2008 | Berdichevsky et al. | |
| 7,613,497 B2 | 11/2009 | Govari et al. | |
| 7,650,192 B2 | 1/2010 | Wahlstrand | |
| 7,738,965 B2 | 6/2010 | Phillips et al. | |
| 7,741,734 B2 | 6/2010 | Joannopoulos et al. | |
| 7,821,230 B2 | 10/2010 | Studyvin et al. | |
| 7,825,543 B2 | 11/2010 | Karalis et al. | |
| 7,825,629 B2 | 11/2010 | Studyvin et al. | |
| 7,825,776 B2 | 11/2010 | Smith et al. | |
| 7,928,691 B2 | 4/2011 | Studyvin et al. | |
| 7,956,725 B2 | 6/2011 | Smith | |
| 8,075,472 B2 | 12/2011 | Zilbershlag et al. | |
| 8,129,865 B2 | 3/2012 | Krumme et al. | |
| 8,244,367 B2 | 8/2012 | Wahlstrand et al. | |
| 8,278,784 B2 | 10/2012 | Cook et al. | |
| 8,285,388 B2 | 10/2012 | Wahlstrand | |
| 8,579,789 B1 | 11/2013 | Zilbershlag | |
| 8,585,572 B2 | 11/2013 | Mehmanesh | |
| 8,840,539 B2 | 9/2014 | Zilbershlag | |
| 8,845,510 B2 | 9/2014 | Zilbershlag | |
| 8,961,389 B2 | 2/2015 | Zilbershlag | |
| 8,979,728 B2 | 3/2015 | Zilbershlag | |
| 9,343,224 B2 | 5/2016 | Zilbershlag | |
| 2003/0163020 A1 | 8/2003 | Frazier | |
| 2004/0014315 A1 | 1/2004 | Lai et al. | |
| 2004/0054251 A1 | 3/2004 | Liotta | |
| 2004/0115038 A1 | 6/2004 | Nuesser et al. | |
| 2005/0220636 A1 | 10/2005 | Henein et al. | |
| 2006/0085039 A1 | 4/2006 | Hastings et al. | |
| 2006/0085041 A1 | 4/2006 | Hastings et al. | |
| 2007/0132587 A1 | 6/2007 | Smith et al. | |
| 2007/0182578 A1 | 8/2007 | Smith | |
| 2007/0255223 A1 | 11/2007 | Phillips et al. | |
| 2008/0041930 A1 | 2/2008 | Smith et al. | |
| 2008/0109054 A1 | 5/2008 | Hastings et al. | |
| 2008/0238680 A1 | 10/2008 | Posamentier et al. | |
| 2008/0292478 A1 | 11/2008 | Baykut et al. | |
| 2009/0243813 A1 | 10/2009 | Smith et al. | |
| 2010/0045114 A1 | 2/2010 | Sample et al. | |
| 2010/0052811 A1 | 3/2010 | Smith et al. | |
| 2010/0076247 A1 | 3/2010 | Zilbershlag et al. | |
| 2010/0081379 A1 | 4/2010 | Cooper et al. | |
| 2010/0187913 A1 | 7/2010 | Smith et al. | |
| 2010/0197994 A1 | 8/2010 | Mehmanesh | |
| 2011/0080051 A1 | 4/2011 | Lee et al. | |
| 2011/0193688 A1 | 8/2011 | Forsell | |
| 2011/0278948 A1 | 11/2011 | Forsell | |
| 2011/0301668 A1 | 12/2011 | Forsell | |
| 2012/0123284 A1 | 5/2012 | Kheradvar | |
| 2012/0146575 A1 | 6/2012 | Armstrong et al. | |
| 2012/0150291 A1 | 6/2012 | Aber et al. | |
| 2012/0235502 A1 | 9/2012 | Kesler et al. | |
| 2012/0239118 A1 | 9/2012 | Ozawa et al. | |
| 2013/0043736 A1 | 2/2013 | Zilbershlag | |
| 2013/0053624 A1 | 2/2013 | Zilbershlag | |
| 2013/0141109 A1 | 6/2013 | Love et al. | |
| 2014/0031607 A1 | 1/2014 | Zilbershlag et al. | |
| 2014/0163307 A1 | 6/2014 | Zilbershlag | |
| 2014/0236172 A1 | 8/2014 | Hastings et al. | |
| 2016/0023004 A1 | 1/2016 | Forsell | |

OTHER PUBLICATIONS

Farmer, J. et al., "Wireless Battery Management System for Safe High-Capacity Energy Storage," 31st Annual Battery Seminar (Orlando, FL), 2014, 4 pages.

Garcia, H.E. et al., "On-line State-of-Health and Remaining-Useful-Life Assessment of Batteries using Rapid Impedance Spectrum Measurements," 45th Power Sources Symposium, Las Vegas, Abstract 7.3, 2012, 4 pages.

International Search Report dated Jan. 30, 2009 for International Application No. PCT/IL2008/000604 (4Pages).

Leviticus Cardio CET System, Youtube.com, available at www.youtube.com/watch?v=ipw7dXPJtvA <http://www.youtube.com/watch?v=ipw7dXPJtvA>, published May 18, 2016 (retrieved Jan. 3, 2018).

Leviticus Cardio webpage, available at www.leviticus-cardio.com <http://www.leviticus-cardio.com> (retrieved Jan. 3, 2018).

Patridge, C.J. & Love, C.T., "Impedance Spectroscopy Diagnostic for Monitoring Li-ion Batteries," 45th Power Sources Symposium, Las Vegas, Abstract 7.4, 2012, 4 pages.

2S2P Cell architecture

ALERTING A PATIENT

CROSS-REFERENCE TO RELATED APPLICATIONS

This application is a continuation of U.S. patent application Ser. No. 15/713,066, filed Sep. 22, 2017, which is a continuation-in-part of U.S. patent application Ser. No. 14/535,528, filed Nov. 7, 2014, now U.S. Pat. No. 9,793,579, issued Oct. 17, 2017, which claims the benefit of and priority to U.S. Provisional Patent Application No. 61/901,751, filed Nov. 8, 2013, the entire contents of which are incorporated herein by reference.

TECHNICAL FIELD

The present disclosure generally relates to the field of batteries and particularly to safety features of batteries for use with implantable medical devices such as wirelessly-powered ventricular assist devices (VADs).

BACKGROUND INFORMATION

A lithium-ion battery (LIB) is a type of rechargeable battery that is widely used in various applications due to its very high energy density compared to other rechargeable battery types. LIBs are commercially available in portable electronics, power tools, electric vehicles, and many other devices.

Commercially available LIBs are generally designed to be charged and discharged at room temperature. Such consumer-targeted LIBs also are designed to safely discharge down to a cut-off voltage of around 2.5-3.0 V.

It is known to use LIBs to power medical implants, such as ventricular assist devices (VADs). Unlike consumer-use LIBs, the LIBs used in medical implants are designed to be charged and discharged at body temperature (around 37° C.). Also, medical implant LIB s typically are designed to discharge down to close to 0 (zero) V. This low cut-off voltage capability for implantable LIB s is a safety feature to protect the LIB s from over-discharge conditions which can damage the LIB cell and lead to its failure.

Although commonly used, LIBs present certain safety hazards. LIBs are particularly susceptible to abuse, which can lead to thermal runaway. Abuse can be external physical abuse, such as puncture, compression, dropping, vibration, or exposure to heat or fire. Abuse can also result from internal causes like over-charging, over-discharging, high rate charge at low temperature, or high or low temperature operation.

Thermal runaway refers to a situation where an increase in temperature causes a further increase in temperature, leading to a dangerous chain reaction. In such conditions, temperatures may quickly rise to unsafe levels, creating a potentially destructive result such as an explosion or fire. Thermal runaway can result from an internal fault, either from improper use or raw material defects.

To prevent dangerous conditions and explosions, consumer LIBs generally have vents, which allow the cell to release excess internal pressure. In the event of an abusive situation, the vents can release vapors of the cell's organic solvent electrolyte. Unlike consumer LIBs, the LIBs for use in implantable medical devices are hermetically sealed and have no vents, due to the damage that would be done to the body if vapors or organic solvent electrolytes escaped from the cell.

For life-sustaining medical devices, battery failure could lead to catastrophic results. For any battery implanted in the body, a battery explosion could do significant harm to the user. Some batteries known in the art are capable of measuring temperature to determine that a fault has occurred. But for critical devices like VADs, once a fault has occurred, it may be too late to mitigate the disastrous health effects.

SUMMARY

A multi-cell battery pack is described that includes certain features for monitoring parameters of a cell to determine when the cell should be disconnected from the pack in order maintain operation of the battery pack while mitigating a dangerous condition in a particular cell. The determination that a cell needs to be disconnected can be based on a parameter of the cell meeting an objective threshold, or it can be based on a comparison between the multiple cells in the battery pack to identify which cell is not operating correctly based on the difference between it and the other cells. When a fault or a predicted fault is identified, the battery pack can be reconfigured to continue operating in a safer mode, generally by disconnecting the problematic cell. The battery pack also includes features for preventing over-charging of the pack when one or more cells has been disconnected so that a standard charger can be used with the battery pack without causing it to overcharge. Additional automatic recovery circuitry allows the cell to be periodically reconnected to the battery pack to determine if its conditions have improved and it is able to be put back online. This additional circuitry also includes components for self-powering the automatic recovery circuit while it is disconnected from the rest of the circuit. the self-powering system receives power from the charger while the battery pack is charging even though the cell it is associated with is disconnected. This removes the need for a secondary power source for powering the additional control circuitry.

In certain aspects, the disclosure relates to an over-charge protection system for a multi-cell battery pack, which prevents the battery pack from overcharging when one or more cells has been disconnected. The over-charge protection system includes a circuit with N cells, wherein each cell has a maximum voltage V. Each cell has a fuel gauge configured to monitor a value of a parameter of the cell. Each cell also has a first transistor controlled by the fuel gauge, and the first transistor is configured to close when the value monitored by the fuel gauge meets a predetermined threshold. Closing the first transistor disconnects the cell from the circuit. The over-charge protection system also includes a unit configured to sense a voltage across the cell and to cause a second transistor to close to bypass the cell when the voltage is greater than a threshold and to open when the voltage is smaller than the threshold, thereby preventing the multi-cell battery pack from charging past the voltage of V(N−1).

Another aspect of the disclosure relates to a system for automatically recovering a shunted battery cell in a multi-cell battery pack and smoothly adding it back into the battery pack. The automatic recovery system includes an oscillator circuit comprising a capacitor configured to store power. The oscillator circuit is electrically connected to a transistor configured to assume an open position to direct current through a battery cell that has been shunted from a circuit comprising a plurality of battery cells; and a closed position when removing the battery cell from the circuit. The oscillator circuit is configured to periodically open the transistor to cause a determination to be made as to whether the battery cell has been reconnected to the circuit. The battery cell may have been reconnected by the fuel gauge, based on certain monitored parameters. The automatic recovery system can be self-powered, in the sense that it receives power from the charger while the cell is disconnected from the circuit, and stores the power in the capacitor. This avoids the need for a separate power source for the cell monitoring logic for each cell in the battery pack.

In a related aspect, a method for mitigating a battery condition in a multi-cell battery pack operating at a desired voltage involves monitoring a value of a parameter for each of the three or more cells in the pack. The values are then compared and it is determined whether the value corresponding to one of the cells differs from the other two (or more) values beyond a predetermined threshold. If the value of one of the cells differs beyond the threshold, that cell can be disconnected from battery pack. In some embodiments, the determination that a cell has reached a certain threshold triggers an alert to a human user, and the human user can make a decision and provide an input in order to control whether the cell is to be disconnected. In the various aspects of the invention, cells can be arranged in series and/or in parallel. For example, the architecture may include two parallel branches, each branch including two cells in series. Shunting a cell in a parallel architecture may involve disconnecting an entire branch of cells.

DETAILED DESCRIPTION

Figure 1:
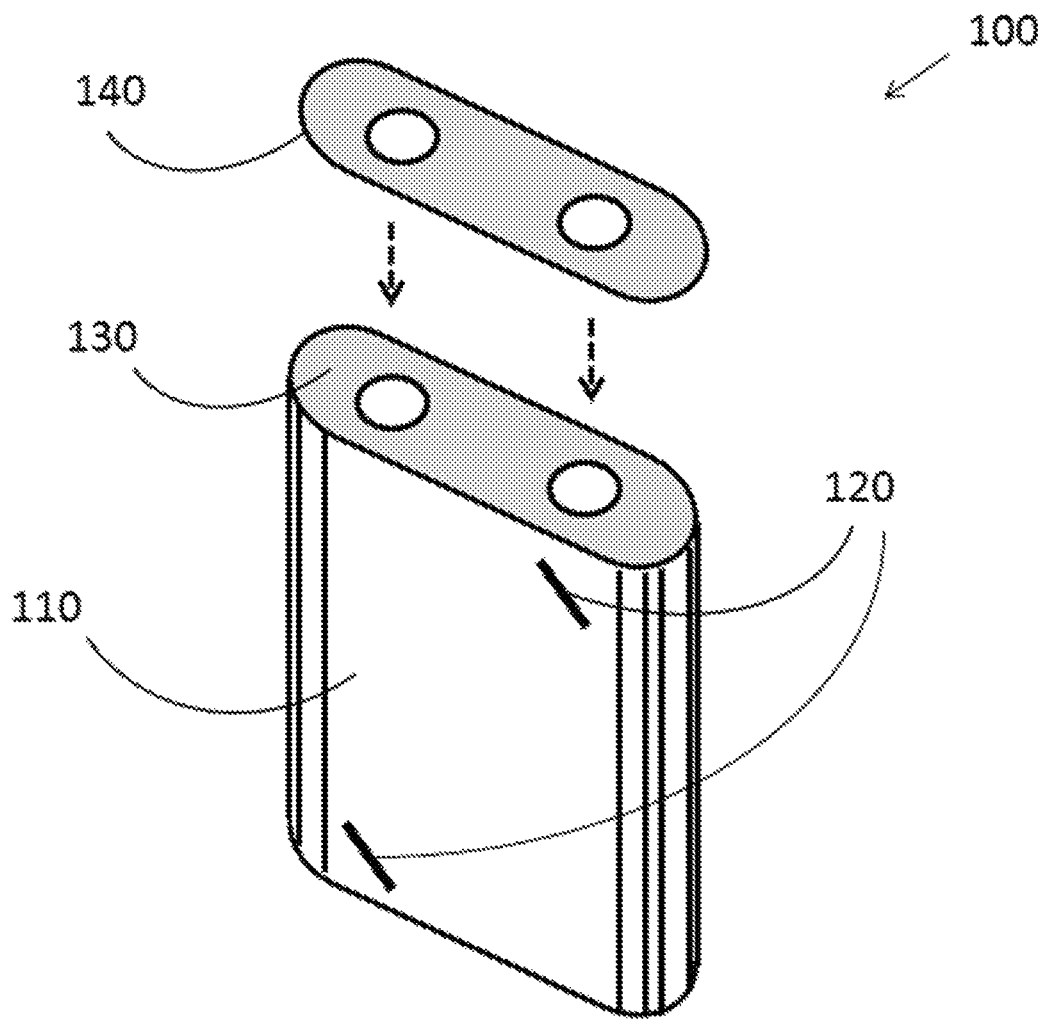
FIG. 1 shows a known rechargeable battery.

Various aspects, features, objects, and advantages of the disclosed innovations will become apparent through reference to the following description and the drawings. Any particular embodiments described herein are not mutually exclusive and can exist in various combinations and permutations even if not specifically indicated herein. Also, various modifications may be made to the embodiments described herein, and the disclosed embodiments and details should not be construed as limiting but instead as illustrative of some embodiments in accordance with the inventions.

A battery according to the present disclosure is capable of identifying a fault or a condition that is a precursor to a fault or that predicts a fault. The fault or pre-fault condition is identified based on the measurement of certain parameters in a cell or cells. Based on one or more measured parameters, the battery may determine that the battery has faulted, is likely to have a fault in the near future, or is experiencing some other error or potential error. The battery may detect that the likelihood of explosion has reached a certain threshold. In response, the battery may reconfigure itself to allow it to continue functioning. It may also trigger an alert, which notifies the user or some other person about the condition so that he or she can take steps to mitigate the potential harm. The alert may involve one or more of: notifying the user to the condition; notifying the user that the battery has reconfigured itself to continue functioning; notifying the user of the amount of time before a fault or explosion occurs; instructing a user that a replacement battery is or will be necessary; instructing the user to supply a backup wireless power source; or instructing the user to connect a wired power source.

The battery may predict a fault situation using inputs from the cells including but not limited to temperature, voltage, current, resistance, charge speed, discharge speed, electrolyte levels, corrosion, environmental conditions, or other measurable parameters known in the art. For example, a multi-cell battery may monitor the temperature of each cell. If a cell reaches a temperature above a certain threshold, but still below the level that would indicate a fault, the battery may respond to that condition by reconfiguring the battery to prevent the potential fault. It may also alert a user about the potential problem. In its reconfigured state, the battery may be able to continue operating at least long enough so that the user can respond to the alert by replacing or supplementing the battery with an external wireless or wired power source. In this way, catastrophic faults or failures can be avoided, as problems with the battery are addressed before they arise.

A battery of the present disclosure can detect conditions indicating that a cell is highly likely to fault (for example, when the probability of fault is greater than 10%, 25%, 50%, 75%, or 90%), and it can also detect conditions that indicate a fault is less likely to occur (for example, when the probability of fault is less than 1%, 0.1%, 0.01% or less). Depending on the severity of the condition and how likely the cell is to fault, the battery may respond in different ways, with different measures of mitigation and different levels of alerts to the user.

The battery response may also be related to the particular type of risk posed by the condition. For example, if the condition of a cell is such that it has a 0.0001% likelihood to explode, the response may be to immediately disconnect the cell and alert the patient to schedule a battery replacement surgery. On the other hand, if the condition of a cell is such that it has a 90% chance to stop working but less than a 0.0001% chance of exploding, the battery may simply reconfigure itself to continue working, but not send an urgent alert to the user about needing a replacement. Alternately, the battery in that situation could do nothing until the cell actually stopped working.

For implanted Lithium-ion batteries in particular, it is vital to avoid explosions and other failures. The present disclosure provides improvements to known batteries, which reduce the likelihood of explosions by notifying user's of dangerous conditions so that the battery can be replaced before the explosion occurs.

FIG. 1 shows an example of a known rechargeable battery 100. The battery casing 110 is typically made from aluminum or steel. The casing 110 has two vents 120 for built-in redundancy. The battery 100 has a current interrupt device 130 at the top of the cell, and a discrete positive temperature coefficient (PTC) device 140. The PTC device 140 is a resistor that increases resistance as battery temperature rises to prevent thermal runaway. In embodiments, a PTC device may be located inside or outside the cell case. It provides a current limiting function primarily for low-current applications, and it can reset itself when the over-current condition is corrected.

Figure 2:
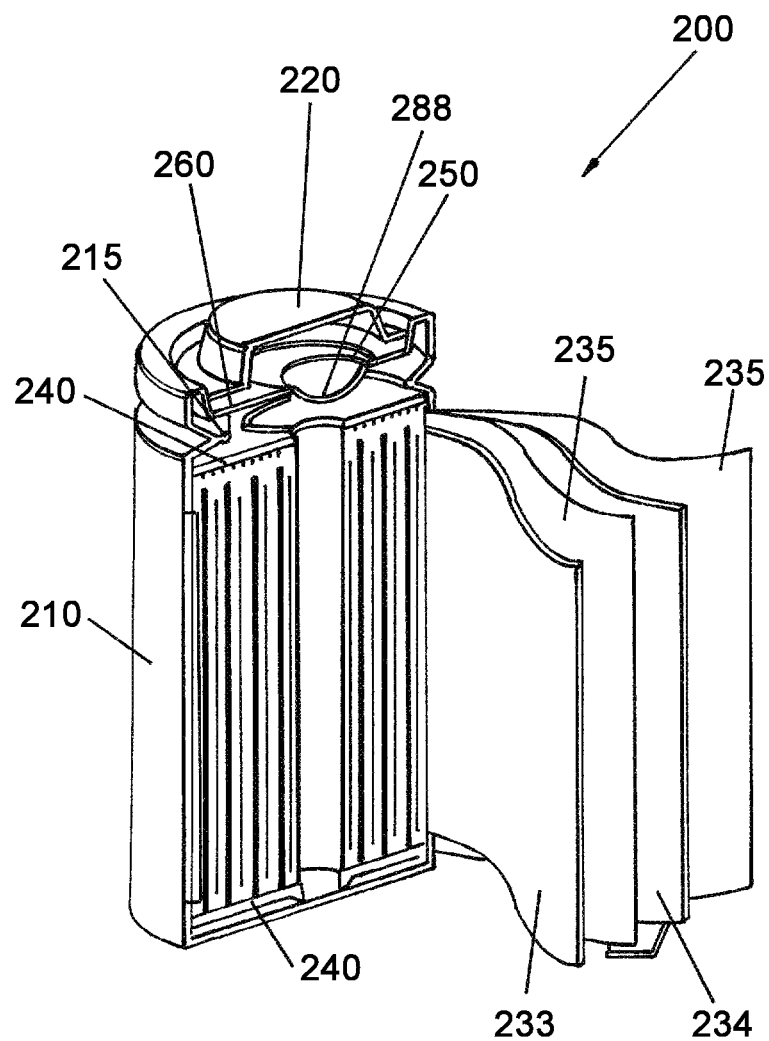
FIG. 2 shows a known lithium-ion battery.

FIG. 2 shows a known lithium-ion battery (LIB) 200, which embodies known safety features. The battery 200 comprises a casing 210 with a positive cap 220 connected with a gasket 215. The casing 210 surrounds cylindrical positive electrodes 233 and negative electrodes 234, with separators 235 in between. The battery 200 features insulation 240 to maintain cell temperature. The battery 200 also features a current interrupt device (CID) 250. If internal pressures get too high, the CID 250 electrically disconnects the cell. The CID 250 acts as a non-resetting circuit breaker. It may comprise a safety valve, an insulating spacer, and a thin metal plate that connects to the electrodes in the cell. When gasses build within the cell, the safety valve deforms, thereby causing it to separate from the thin metal plate. Once the safety valve and thin metal plate have separated, the electrode is disconnected from the exterior can and current can no longer flow. Other safety devices in the battery 200 are a PTC device 260, and a gas release vent 288.

Figure 3:
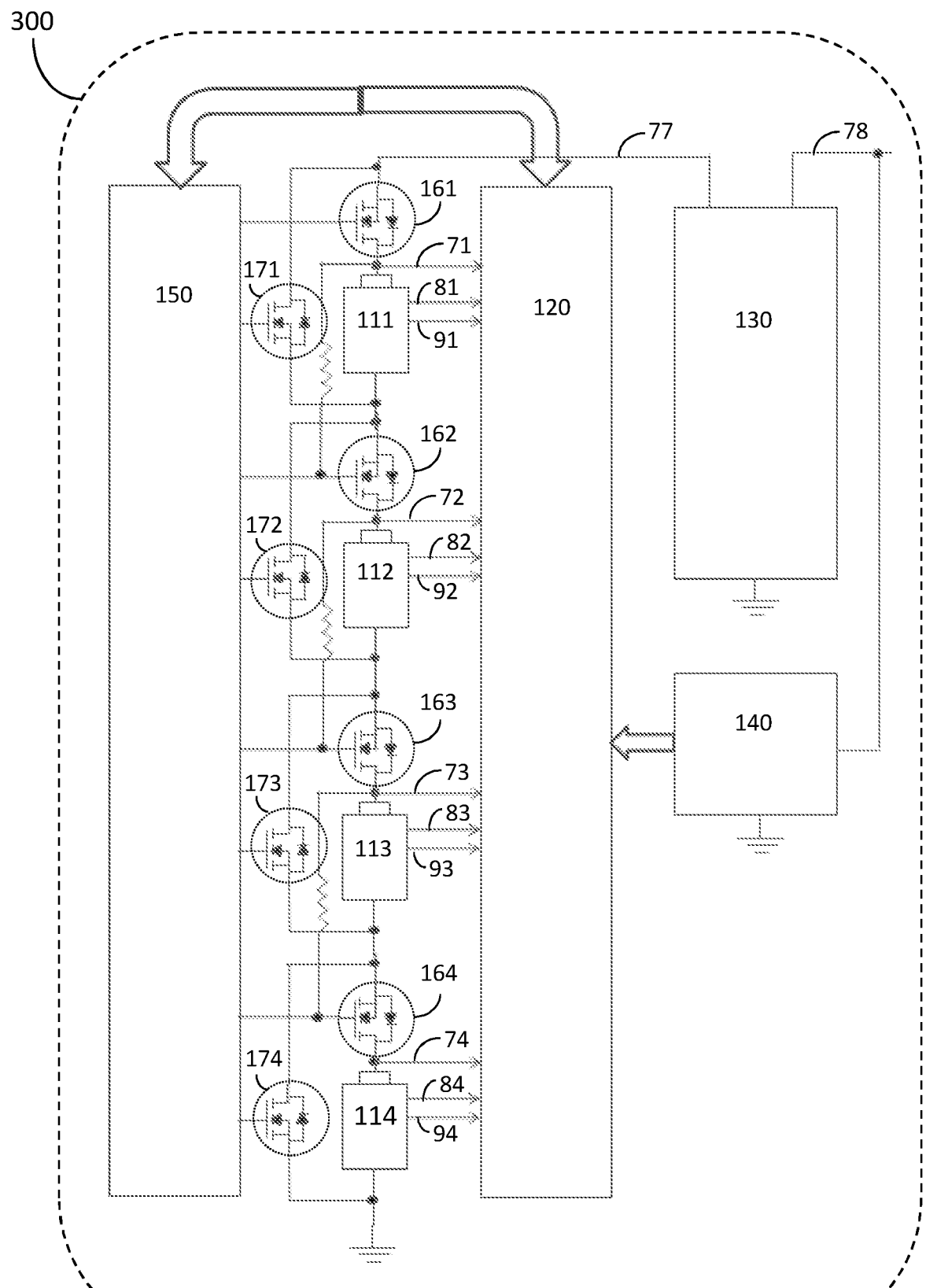
FIG. 3 shows a diagram of a battery system according to the invention.

FIG. 3 is a schematic diagram showing an embodiment of a battery system 300 capable of balancing voltages in response to a fault condition. The system 300 includes four lithium-ion cells 111-114 connected in series. In an embodiment, these can be the 18650 cylindrical-type cells with a nominal voltage of 3.7 V. Other embodiments may include different types of cells, or may include fewer than or more than four cells.

Embodiments of the battery 300 may include various cathodes, anodes, and electrolytes known in the art. For example, the cathode may comprise lithium cobalt oxide ($LiCoO_2$), lithium nickel manganese cobalt oxide ($Li[Ni_x Mn_y Co_z]_2$), lithium nickel cobalt aluminum oxide ($Li[Ni_x Co_y Al_z]_2$), lithium iron phosphate ($LiFePO_4$), lithium manganese oxide ($LiMn_2O_4$), or any other material known in the art. The anode may be graphite or another suitable material. The electrolyte may comprise for example ethylene carbonate, dimethyl carbonate, diethyl carbonate, or a mixture thereof, along with a conducting lithium salt such as $LiPF_6$, $LiBF_4$, $LiAsF_6$, $LiCF_3SO_3$, or $LiClO_4$.

The battery-management system (BMS) 120, also known as a controller unit, receives voltage 71-74, temperature information 81-84, and resistance information 91-94 from each cell 111-114. The software of the BMS 120 can be configured to detect when one cell is getting too hot compared to the other cells. It can then respond by isolating the faulty cell from the others, rebalancing the voltages, or taking other steps to mitigate the situation before a thermal runaway or other problematic event can occur. The hardware of the BMS 120 may include thermal sensors, voltage sensors, current sensors, as well as electronic safety circuits that control the charging and discharging of the cells. The BMS 120 measures various cell parameters including current and voltage during operation and the software can determine the state of charge of the cells. In embodiments, the BMS 120 is configured to recognize when a parameter has reached a certain threshold indicative of a pre-fault condition, and respond by taking steps to prolong the operating life of the battery, while simultaneously notifying the user to find another power source.

The transistors can be metal-oxide-semiconductor field-effect transistors (MOSFETs) or any other transistor known in the art. The load switch or driver 150 is on the high side, meaning that it connects the cells to an electrical load, or disconnects them from it. It is coupled to a controller 120, which sends a signal to the high-side driver 150 based on inputs 71-74, 81-84, and 91-94, for example, from cells 111-114. If the controller 120 determines, for example, based on the inputs of cell 111 that there is a fault or there is a potential future fault, the controller signals the high-side driver to electronically isolate or turn off the defective cell 111 by turning off the N-channel MOSFET switch 161.

In one embodiment, the remaining cells 112-114 provide energy to an electronic device (not shown) such as a ventricular assist device (VAD) at the lower voltage that resulted from one cell being turned off. In such embodiments, the VAD would have been designed to accept the lower voltage for operation. Optionally, the system 300 comprises a DC/DC converter or voltage booster 130. If one or more cells are isolated by the BMS 120 due to faults or potential faults, the voltage booster 130 ramps up the voltage of the remaining cells to maintain a normal power level to the VAD or other device. The controller unit 120 performs cell voltage balancing to keep all the cells in a battery pack at close to the same voltage so as to avoid a destabilizing over-charge. In some embodiments this may be accomplished by using switching shunt resistors across the cell to bring high voltage cells into line with the other cells in the pack. The output voltage is maintained at a level required by the boost converter 130, as long as one or more cells are active. This redundant cell design allows the battery to maintain its normal output level in a fault situation. In some embodiments the battery is designed to be able to continue functioning with one or more cells turned off. In other embodiments the battery can continue functioning for only a short time with one or more cells turned off.

In another embodiment of battery system 300, one of the cells is a reserve cell, which can be connected via a shunt (not shown). The reserve cell can be a backup or spare cell, which is not in use during regular operation of the battery. Alternatively, the reserve cell can have a regular function of powering auxiliary electronics of the VAD or other device. When one of the cells 111-114 fails and has been isolated by the operation described above, the reserve cell is switched on and brought into the series by activating the shunt. In embodiments where the reserve cell's normal function is to provide auxiliary power, the controller 120 assesses the failed or isolated cell to determine whether it is still capable of powering the auxiliary electronics. If it is, the controller 120 proceeds to switch that cell and the reserve cell, so that the reserve cell comes into series with the other active cells to provide power to the device, and the failed cell provides power to the auxiliary electronics. If the failed cell is incapable of powering even the less demanding auxiliary electronics, it remains isolated and the pack of functioning cells is used to power the device and the auxiliary electronics.

In some embodiments the controller 120 can attempt to revive a failed cell by charging it, via slow charge, pulse charge, or another type of charge known in the art. For implantable electronic devices, the type of charge should be compatible with use inside the body. For example, fast charging that results in excessive temperature increase may not be desirable in some embodiments. In embodiments where the cell has not yet failed, but has been determined to be in a pre-failure condition, that pre-failure cell may be revived by the controller 120 in the same manner as described above.

The present disclosure also provides an alert system for notifying the user when a battery fault has occurred or will potentially occur. Systems of the invention provide differentiable alerts for faults or potential faults of different severity. For example, a small or insignificant fault may trigger a minor alert to keep the user apprised of the battery's condition, whereas a more severe fault may trigger a more emphatic or even painful alert, such as a shock, that underscores the gravity of the fault. Alerts can correspond to potential faults of varying degrees as well.

Figure 4:
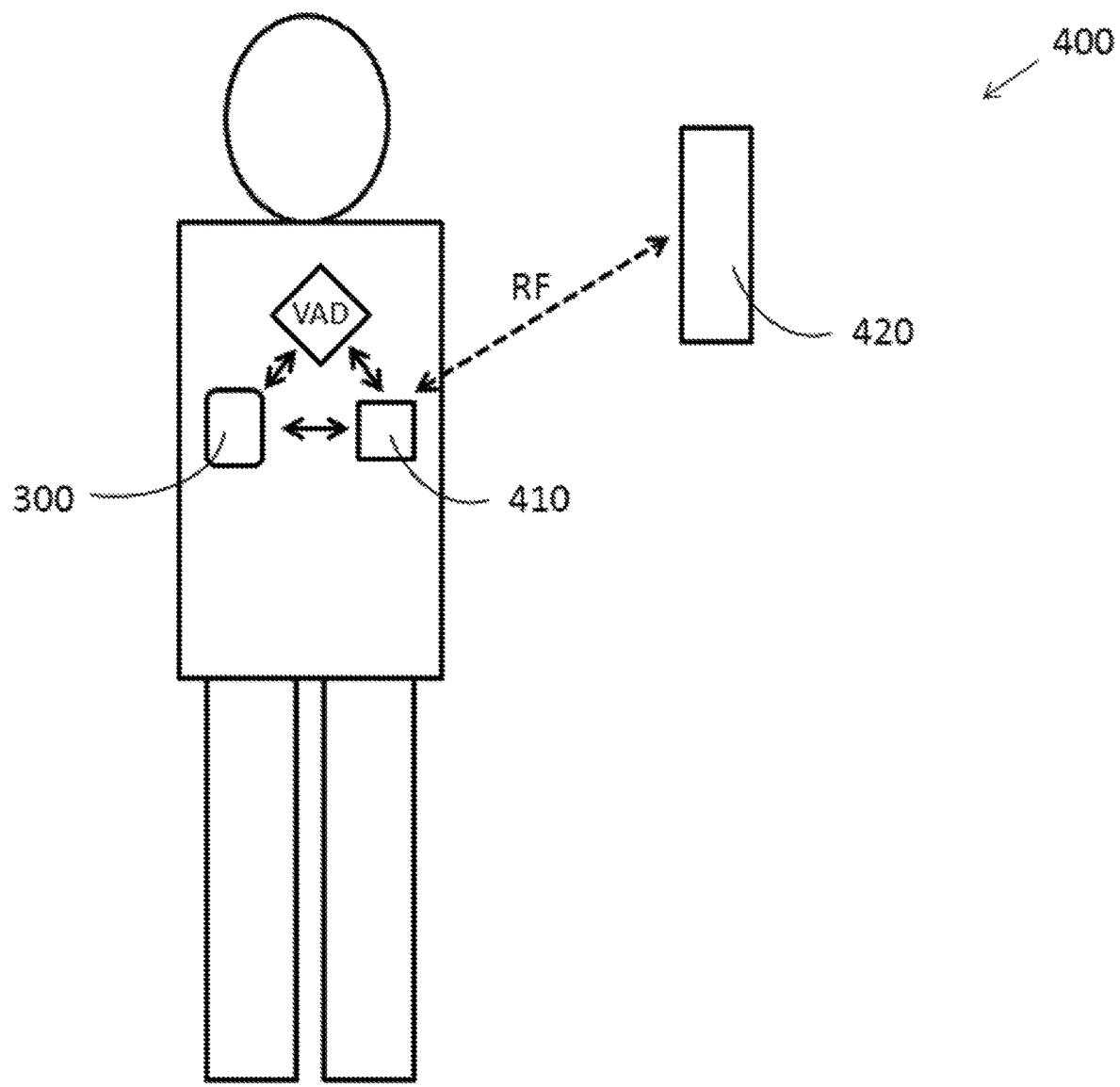
FIG. 4 shows a system for alerting a user to a battery fault using a radio-frequency signal.

FIG. 4 depicts an embodiment of an alert system 400 for alerting a user to an error or a potential error in an implanted battery connected to an implantable electronic device such as a VAD. The error can be a battery fault or another error in the device, or it may be a condition that the BMS has determined is a likely precursor to a fault or other error. The VAD is in electrical communication with a battery system 300 and with an internal controller 410 that is implanted in the user's body. An external controller 420 can be situated outside the user's body. The external controller 420 is capable of receiving radio frequencies from the internal controller 410. In the event of a minor fault or potential fault in the battery 300, a signal is sent to the external controller 420. The external controller 420 may activate a sound, a vibration, or any other indication that can be perceived by the user. In the event of a minor fault where the battery 300 is still functional, the internal device is capable of sending the RF signal. Therefore, this system is ideal for reporting minor faults, potential future faults, or any fault that does not cause the device to shut down completely. Upon perceiving the alert, the user may take an action such as recharging the battery or scheduling a surgery to replace the battery.

More severe faults or potential faults may have a different type of alert. The differentiation between minor and major faults or potential faults helps the user determine what response, if any, is needed. Also, if the condition constitutes a life-threatening emergency, the alert should be comparably acute. For severe errors, the alert should be sufficient to wake the user if necessary.

Figure 5:
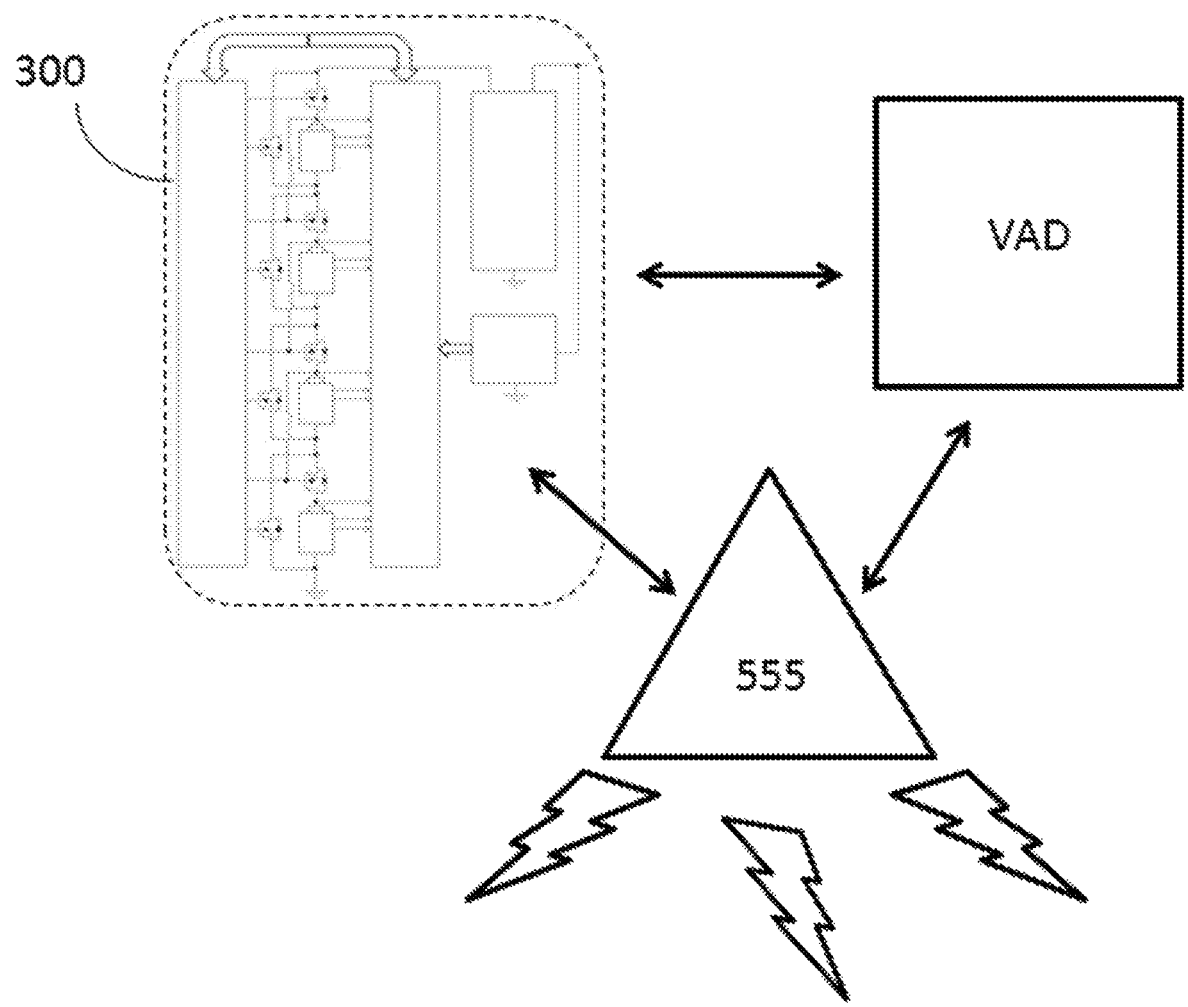
FIG. 5 shows a system for alerting a user to a battery fault including a capacitor.

The present disclosure provides an elevated alert for more serious faults and potential faults. The alert can be a strong vibration, an electrical shock, or another jarring sensation to the user. FIG. 5 depicts a system 500 with a configuration including a battery 300, a VAD, and a separate power source 555. In the event that the battery 300 fails completely and is no longer capable of providing power at all, the separate power source 555 is activated to produce an alert. The power source 555 can be a capacitor compatible with medical implants, such as the KEMET C2220X104K2RACTU capacitor available from Newark Corporation (Chicago, Ill.). An important safety feature of the disclosure is that in the event of a major error or fault in an implantable electronic device, an alert can still be sent, owing to the separate and independent power source 555.

The alarm generated by the power source 555 can be triggered by the power level of the battery falling below a threshold. The threshold can be measured using a comparator. If the battery level drops to the predetermined threshold, the capacitor triggers an electrical shock to notify the user. In another embodiment, the capacitor activates an internal vibration that can be felt by the user. The system may have a variety of alerts, each corresponding to a different type or level of fault.

Figure 6:
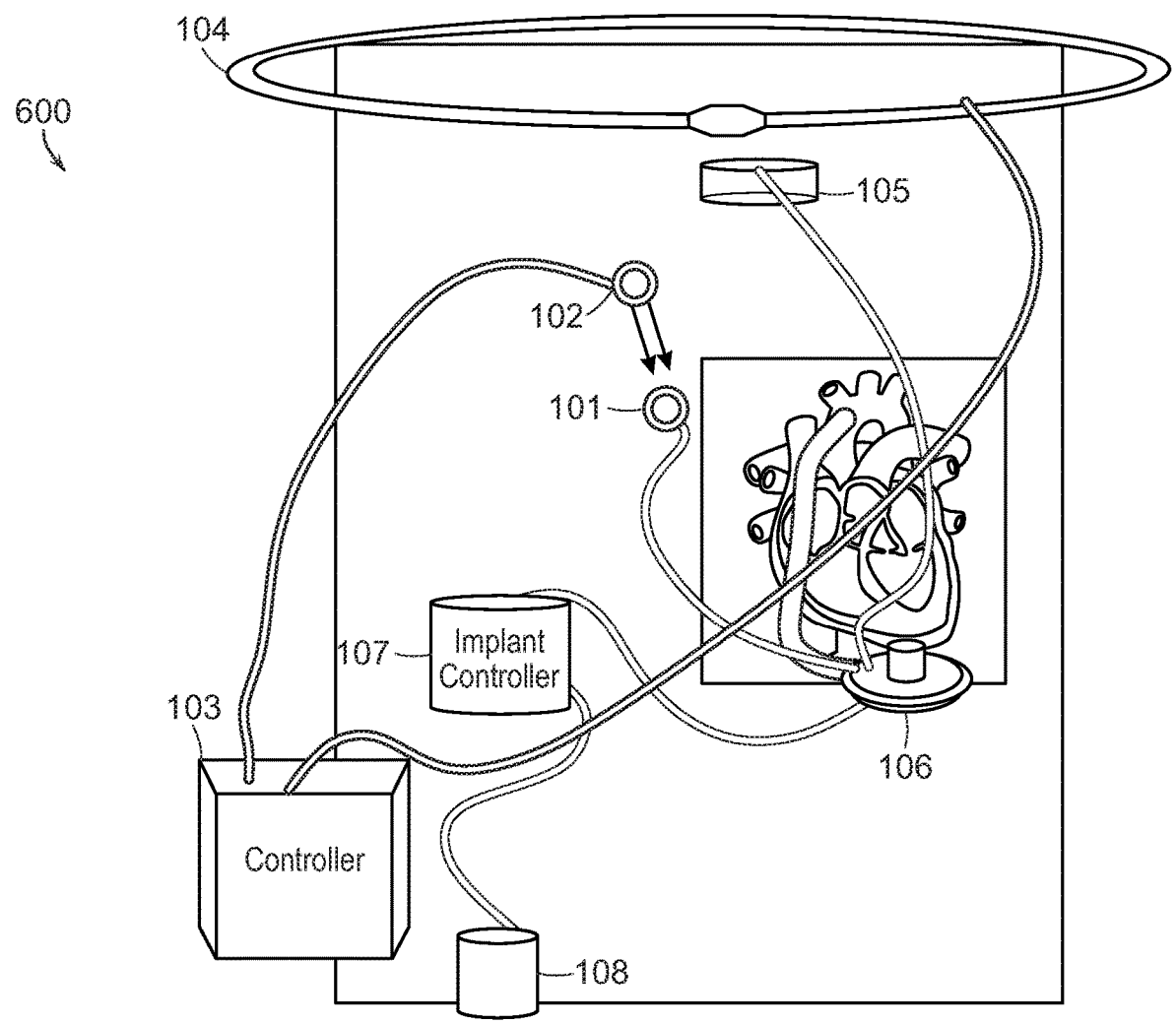
FIG. 6 shows a backup power system.

In the event of a severe or catastrophic fault wherein the user must immediately seek backup power for the device, the system can include external wired or wireless power source. Examples of backup power sources can be found in U.S. Patent Publication 2013/0053624, filed Aug. 22, 2012, the contents of which are incorporated herein in their entirety. FIG. 6 depicts a power transfer system 600 that can be used with the present disclosure as a backup power source. The system 600 includes a power transfer belt 104 connected to an external controller 103, which provides power to the power transfer belt 104. The wireless backup power source can be a wearable device such as a belt or a transfer vest, or it may constitute any other suitable configuration. As shown, the power transfer belt 104 can provide wireless power transfer to the internal power receiver 105, which is connected to an implanted electronic device 106.

The system may also comprise a wired external power source, which can be separate from or connected to the wireless power source. In FIG. 6, the external power transfer system 600 comprises an external male unit 102 with prongs, which can be inserted through the skin and coupled to an implanted female unit 101. The male unit 102 is connected to the controller 103, and the female unit is connected to the implanted device 106. Thus, the connection between the male unit 102 and female unit 101 creates a wired connection between the implanted device 106 and the controller 103, which provides power. The external power source may have a feature that communicates to the internal battery to shut off in the event that the internal battery is continuing to function.

In some embodiments, both a wireless and a wired external power source are provided for backup power. In other embodiments, only one or the other is provided. In some embodiments, the wireless external power source is a primary backup power source, and the wired external power source is a secondary backup power source for when the primary backup fails.

In addition to monitoring battery conditions and alerting the user, the present disclosure provides additional safety features that can be used in conjunction with or separately from the safety features described above. FIGS. 7-13 depict various embodiments of improved battery casings for implantable LIBs. Unlike known implantable batteries, which exclude vents due to the potential bodily harm that could result from venting within the body, the present disclosure reveals designs for battery casings that allow venting to safely occur. These casings prevent explosion or other problems associated with increased pressure in a battery, while minimizing risk to the user.

Figure 7:
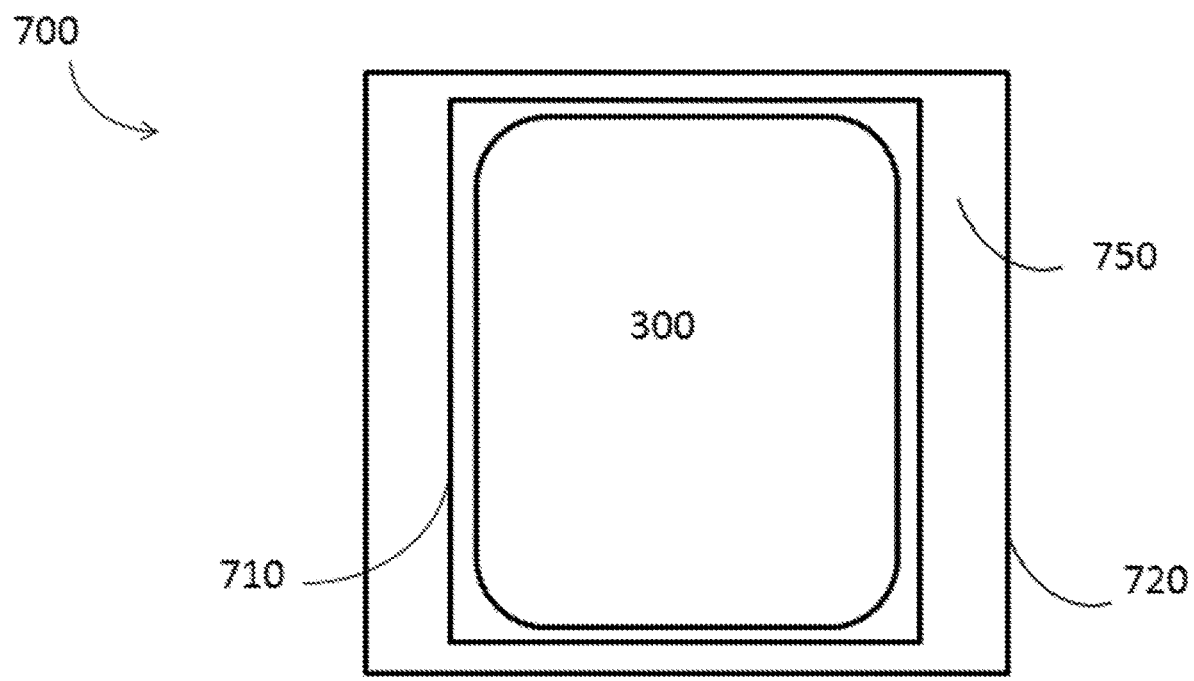
FIG. 7 shows a double-walled battery casing.

FIG. 7 shows a schematic view of a device 700 including a double-walled battery casing. The battery 300 is surrounded by an inner wall 710, which is situated within an outer wall 720. There is a vacuum 750 in between. The walls 710 and 720 can be made from aluminum, steel, stainless steel, titanium, titanium alloy, or any other suitable material known in the art. The double-walled design provides added protection against pressures that build up inside the battery unit 300 when cells vent.

The vacuum 750 has a stabilizing effect on the temperature of the battery. In a normal implanted battery pressure may increase as temperatures rise. However, the vacuum 750 surrounding the battery 300 mitigates the pressure increase that would otherwise result from the hot vapors. The vacuum 750 insulates the battery from the outside, preventing an increased temperature in a fault situation from causing discomfort or burns. It also can allow the cells to maintain a temperature below body temperature, so that the battery does not necessarily have to be configured to operate at about 37° C. Additionally, the battery experiences less of a temperature rise on charging, making it more efficient and allowing for fast charging. In embodiments that include a PTC device, the vacuum 750 makes PTC device less likely to activate, thereby prolonging the life of the cell.

Figure 8:
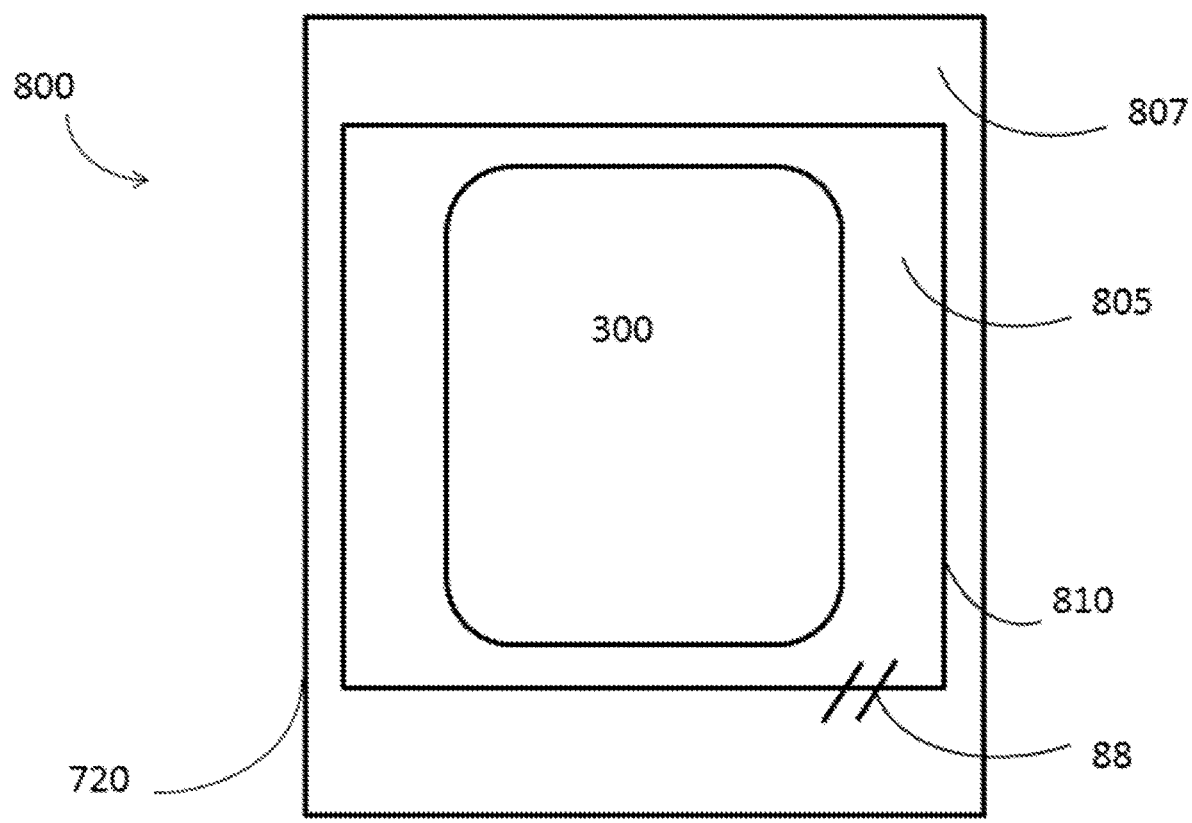
FIG. 8 shows a battery casing with a dividing wall and a vent.

In an embodiment of the casing depicted in FIG. 8, the controller case is divided into two sections by a dividing wall 810, and the dividing wall 810 has its own vent 88. The first section 805 is defined by the dividing wall 810. The second section 807 is a reservoir for the vent pressure. When a cell or cells vent, and the pressure increases inside the first section 805, the danger of the case bursting and releasing organic solvent into the body is minimized because the vent 88 in the dividing wall 810 will open and release the vapors into the second section 807.

Figure 9:
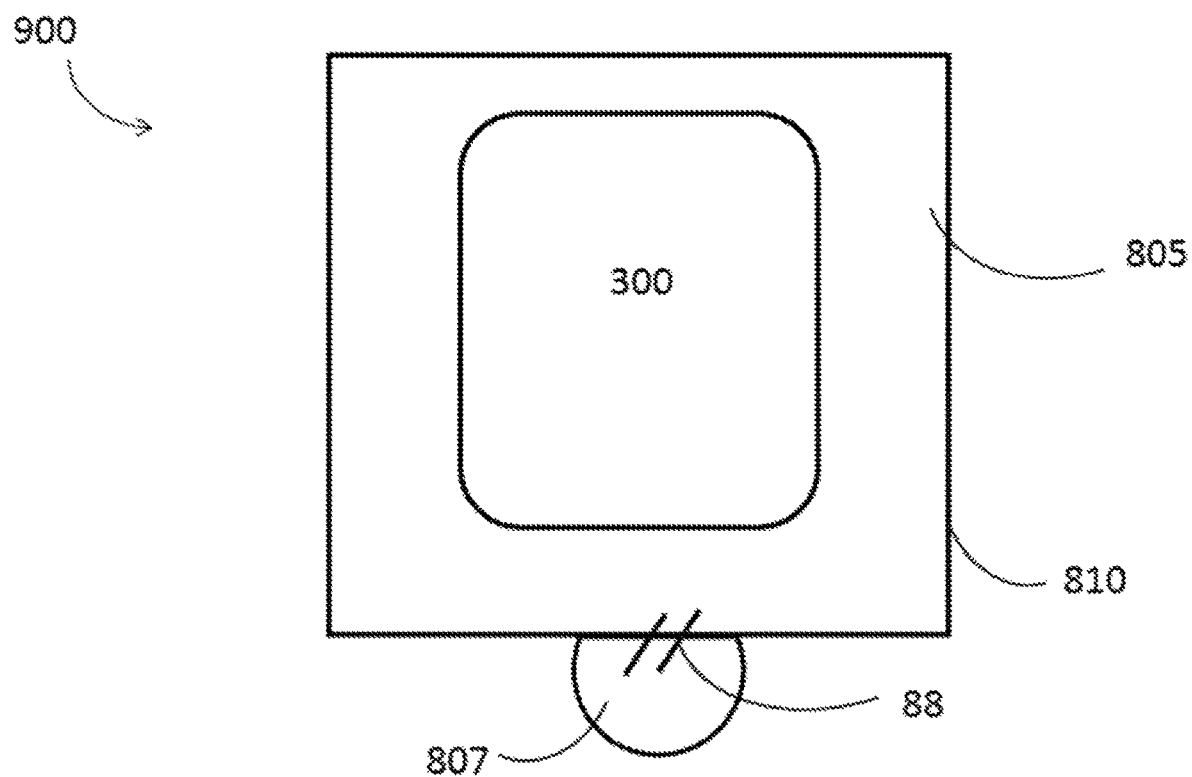
FIG. 9 shows a battery casing with a reservoir section.

FIG. 9 shows another embodiment capable of mitigating extreme pressure differences by directing the first section vent into reservoir section 907 that is an inflatable high volume balloon. When pressure inside the first section 805 increases, the vent 88 may open, releasing organic solvents into the inflatable reservoir section 907. Because the reservoir section 907 is also deflatable, it may reduce in size as the released vapors eventually cool.

Figure 10:
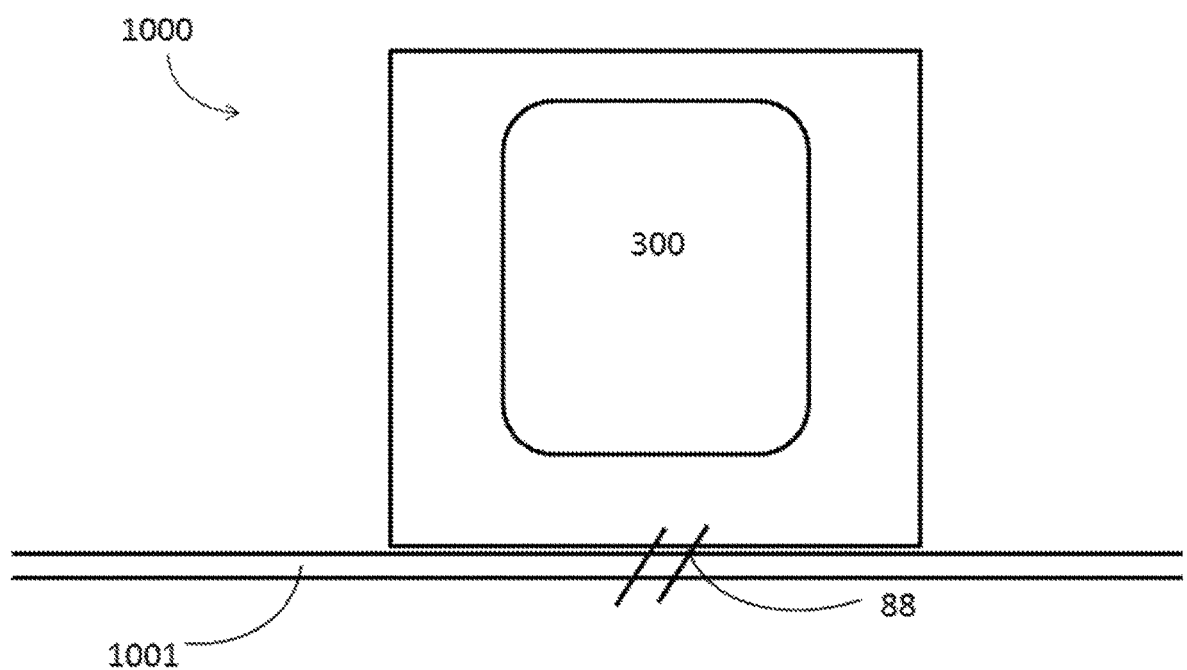
FIG. 10 shows a battery casing with a vent capable of directing vapors outside the body.

FIG. 10 shows a controller casing 1000 including a vent 88 that directs vapors to the outside of the body. In the configuration depicted in FIG. 10, the casing is implanted near an external surface 1001 of the body. This embodiment may be considered a last-resort for relieving a faulty battery from pressure buildup. The vent 88 is configured to break through the skin and release the pressure outside the body. In extreme situations, it is dramatically better to direct the damage to the skin rather than to internal organs.

Figure 11:
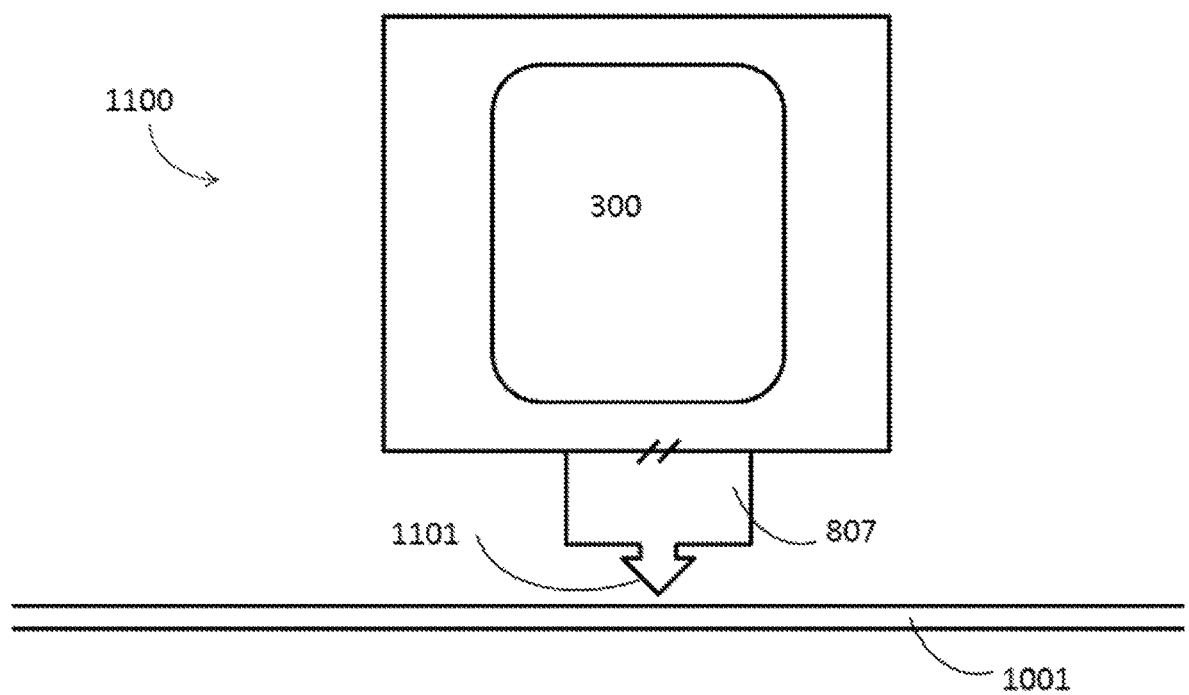
FIG. 11 shows a battery casing with a reservoir section that includes a sharp header.

FIG. 11 shows an embodiment wherein the inflatable reservoir section 807 comprises a sharp or arrow-like header 1101 that is positioned to break the surface of the skin and release pressure outside the body. The section 807 may be configured to break open to release organic solvents once it has broken through to the outside of the body.

In another embodiment, the battery is located within a flexible casing envelope. When vapors are vented, they collect in the envelope. The envelope prevents harmful vapors or liquids from coming into contact with the body. The electronic circuitry in the control unit, whether located in the same section as the battery pack, or in the second section, can be encased in a polymer or other material to isolate it and prevent it from being damaged by any organic solvent vapors or liquids that are vented by the cells.

In other embodiments, insulating materials can be used to protect parts of the battery. Thermal insulation can be inserted between cells to thermally isolate them from each other. The cells can also simply be physically separated by air or a vacuum to prevent direct conduction of heat between them. In other embodiments, cells are divided by insulating plates comprising foam, ceramic, carbon composites, silica fiber tiles, glass fiber insulation, or the like.

In other embodiments, a heat pipe or heat pin can be used to cool the batteries. The heat pipe controls the transfer of heat between surfaces using thermal conductivity. It can be filled with a solvent whose boiling point is slightly greater than body temperature like cyclopentane (49° C.), dichloromethane (40° C.), acetone (56° C.), or methylene chloride (40° C.).

In other embodiments, an absorbing material can be included in the control unit to absorb any leaked or vented organic solvent. Without implying any limitation, absorbing materials may comprise vermiculite in granular or other form, absorbing paper (non-woven or woven) or fibers, sawdust, and the like.

As described above, battery packs can be designed with cell fault detection features. A faulty cell can be detected and disconnected, while the remaining cells are adjusted in order to maintain the appropriate voltage and function of the battery. FIGS. 12-15 show embodiments of how to achieve that reconfiguration of cells. The particular battery pack designs are able to detect a malfunctioning cell and reconfigure the battery to continue performing with the remaining functional cells. Identifying a battery condition that indicates or predicts failure allows adjustments to be made which mitigate the potentially dangerous conditions and allow the battery to continue operating. The battery is able to turn off, isolate, or otherwise disable a problematic cell and adjust the voltage of the remaining cells to compensate.

Figure 12:
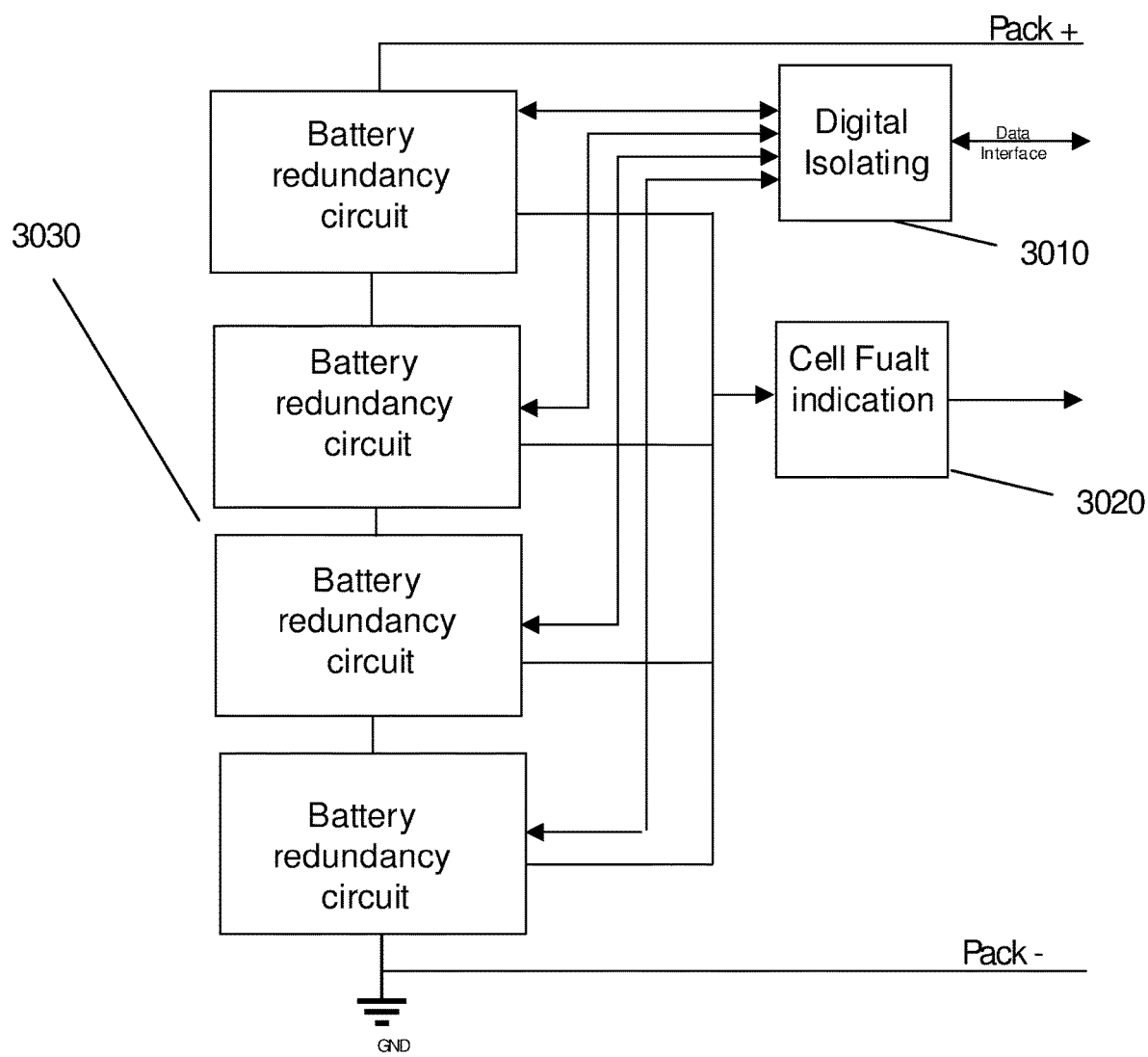
FIG. 12 shows a battery pack diagram.
Figure 13:
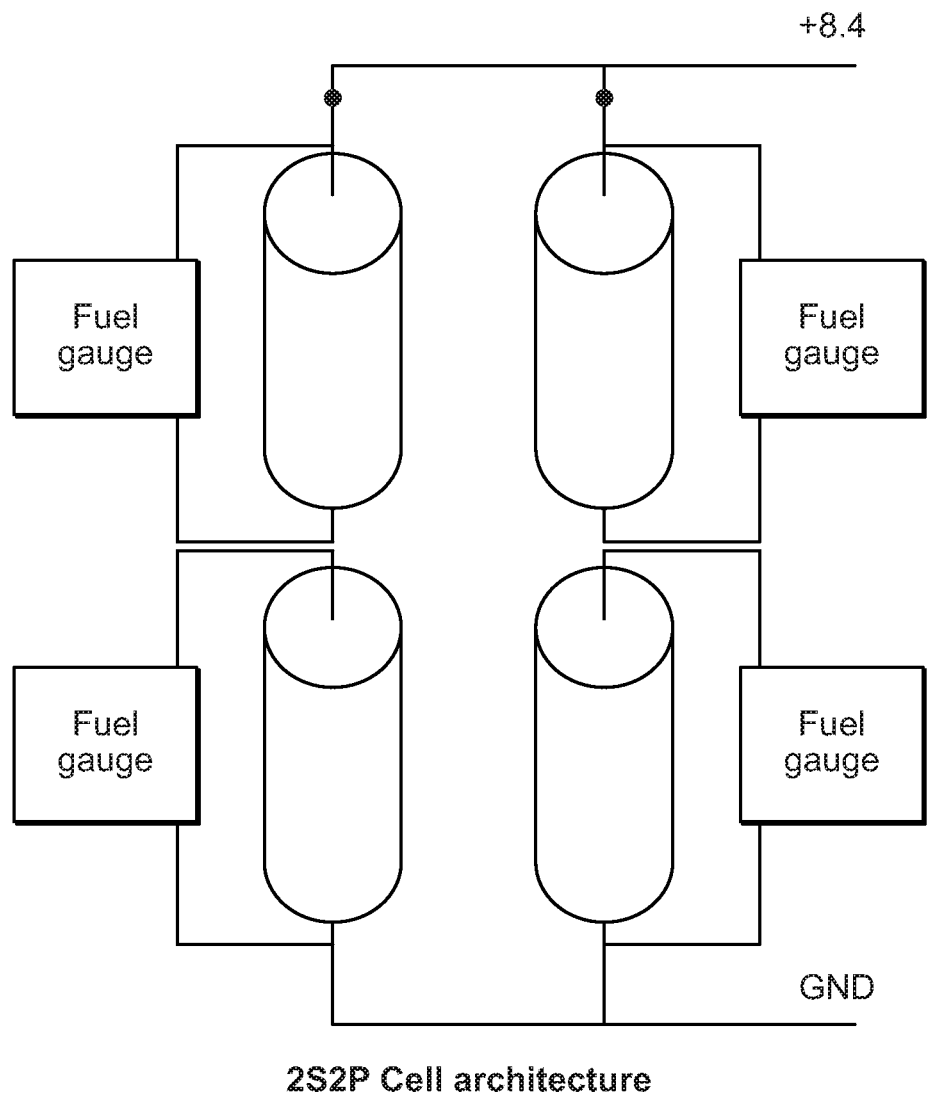
FIG. 13 shows a battery pack diagram with parallel cell architecture.

FIG. 12 is a schematic diagram showing one embodiment of a battery with a series of cell redundancy circuits 3030. The battery can have any arbitrary number N of cell redundancy circuits that form an N-cell pack LIB. In the example shown, the battery is a 4-cell pack. In a particular embodiment, the cells have a maximum voltage of 4.2 V. Other embodiments may include cells with lower or higher voltages, but the following disclosure will assume the cells are designed to have a voltage of 4.2 V. The embodiment of FIG. 12 therefore shows a circuit that provides a 16.8 V charge. Using 4.2 V cells, the charging system is set to the maximum voltage of N×4.2 V. Additionally, different numbers of cells can be used, and the cells can be connected in series or in parallel, depending on the particular needs of the battery. FIG. 13 for example shows a configuration of two parallel series of two cells each (referred to as "2S2P" architecture). In this parallel architecture, a cell or even a full branch of the parallel structure can be disconnected when a cell in that branch fails. Due to the parallel architecture of the embodiment shown in FIG. 13, the voltage drop across the battery is only 8.4 V rather than 16.8 V. Just as in the serial structure, each cell in the FIG. 13 is connected to a fuel gauge for predicting when a cell has failed or is likely to fail. The parallel architecture may be desirable over a serial architecture in some embodiments to simplify the mechanism for handling a cell failure.

Returning to FIG. 12, the bottom-most cell is connected directly to the charger GND and has the voltage range from ground-to-4.2 V. The second cell's voltage is from 4.2 V to 8.4 V. The third cell's voltage is from 8.4 V to 12.6 V, and the fourth cell's voltage is from 12.6 V to 16.8 V. The Cell '−' of one cell is the Cell '+' of previous cell. Accordingly, each cell operates in a different voltage domain.

The data interface of each cell is therefore connected to a digital isolating mechanism 3010, which operates to normalize the cells operating in different voltage domains to the same ground, which allows the pack to aggregate multiple digital buses with different DC domains to a single, shared communication bus. As shown, the first cell already has the same ground as the controller, but the others are operating at higher voltages. Digital isolator 3010 gets them all back down to the shared ground, for connecting with the controller. The digital isolator 3010 can be built from four off-the-shelf inter-integrated (I2C) circuit bus chip, such as the LTC4310IDD, available from Linear Technology (Irvine, Calif.). In the embodiment shown, unit 3010 has three channels (one for each of the cells operating at higher voltage), each of which uses two LTC4310IDD chips. The cell fault indication unit 3020 is an optional direct logic indicator of cell failure connecting different DC domains.

On a standard charging circuit that charges up to 16.8 V, when one cell is disconnected, the others would be overcharged. However, as presently disclosed each cell includes a bypass and recovery unit which rebalances the charges and solves that problem, as explained below with reference to FIG. 14. Being able to shunt a cell to avoid overcharging the others is a unique feature to the disclosed structure. A cell can be isolated or removed and the fixed voltage charging system is still able to charge the battery.

Figure 14:
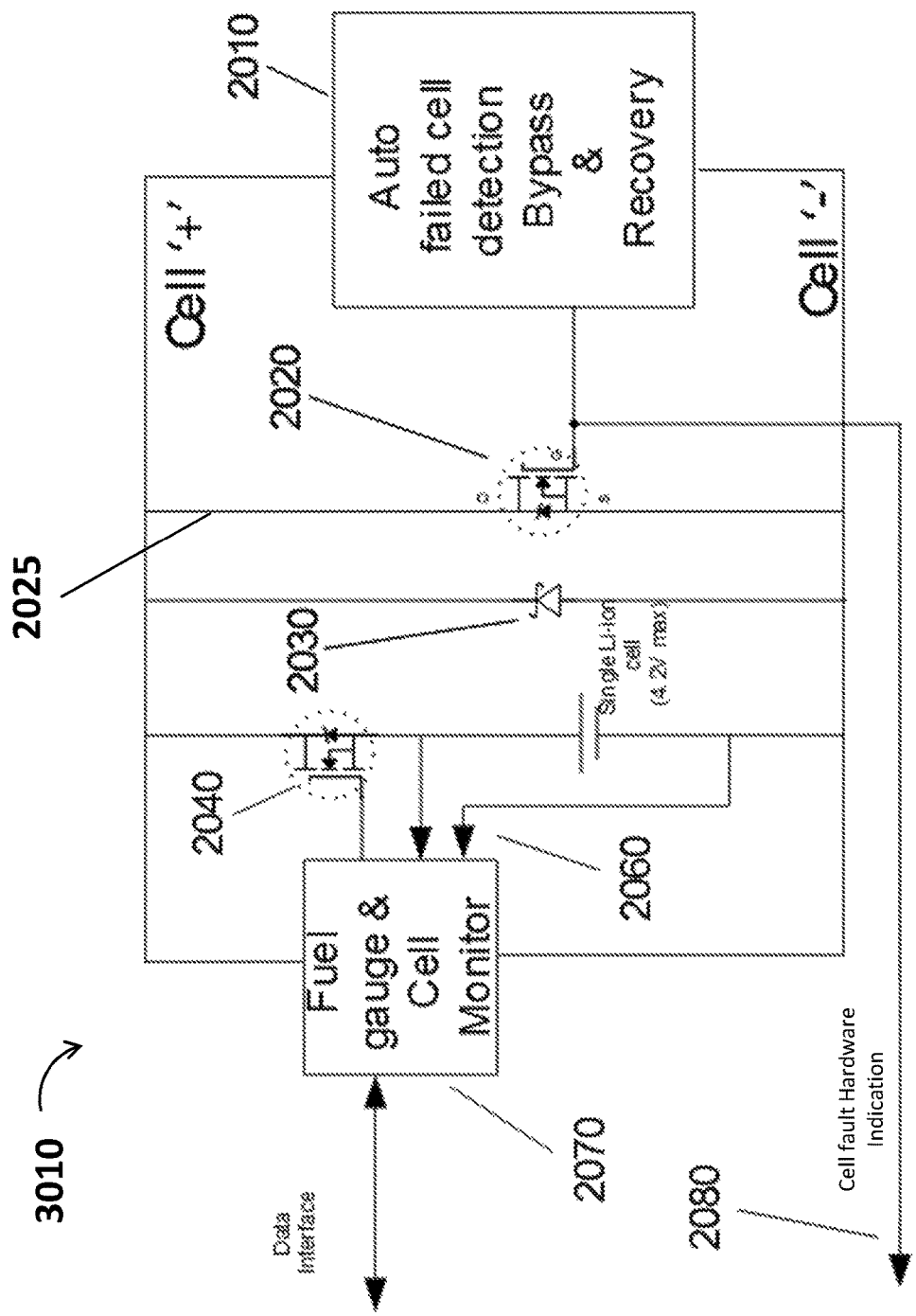
FIG. 14 shows a cell redundancy circuit.

Each of the cell redundancy circuits 3030 includes the circuitry shown in FIG. 14, which includes a fuel gauge 2070 in parallel to the cell (labeled Single Li-ion cell). The fuel gauge 2070 monitors the Li-ion cell by sensing the relevant data and relaying it via a data interface to a controller (not shown), which contains software for determining whether the cell is operating properly or needs to be disconnected. The fuel gauge 2070 can therefore cause the cell to be disconnected automatically if a threshold is reached, such as an overcharge threshold or a threshold of any of the other measured parameters, as determined by the software of the controller. If, for example, the controller determines an overcharge threshold is reached, the fuel gauge 2070 causes transistor 2040 to disconnect the cell.

Figure 15:
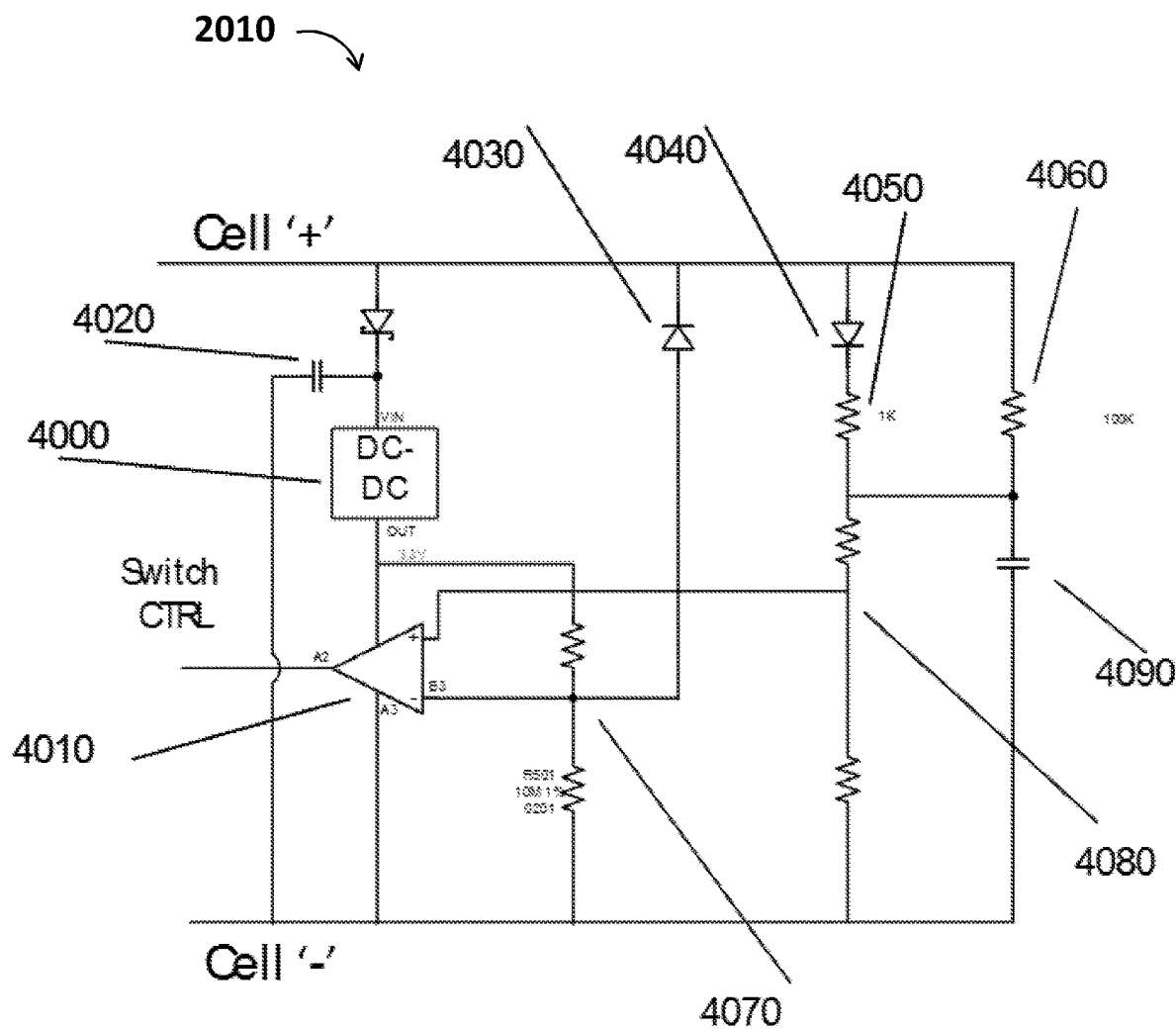
FIG. 15 shows the circuitry of the bypass and recovery module.

When transistor 2040 disconnects the cell, unit 2010 senses a high voltage due to the cell having been removed, and it triggers the bypass of the cell using transistor 2020. Then, while the cell is disconnected, unit 2010 monitors the disconnected cell and periodically reassesses the cell by opening and closing transistor 2020 to see if the cell was reconnected by the fuel gauge 2070. The circuitry within unit 2010 for oscillating the transistor 2020 between open and closed is shown in FIG. 15. When transistor 2020 is closed, the wire 2025 allows current to flow through, bypassing the battery cell. The cell is removed from the circuit by transistor 2040. When transistor 2020 is open and transistor 2040 is closed the Li-ion cell is connected to the circuit. Unit 2010 determines when the current should be shunted through line 2025 by closing switch 2020. The logic contained within unit 2010 for making that determination is shown in FIG. 15. In general, unit 2010 functions by monitoring a specific cell terminal voltage to determine whether it is greater than a particular threshold as described above. When a cell is disconnected (either automatically by the fuel gauge monitor and protection mechanism or by the host software controller when cell failure has been predicted), the transistor 2020 is closed, shorting the disconnected cell output terminals while the other cells in the pack remain charged. Unit 2010 periodically opens transistor 2020 in order to recover the cell connection if the cell has been re-connected by the fuel gauge (either automatically or by host software control). Unit 2010 acts as an automatic recovery mechanism that allows a disconnected cell to be smoothly added back into the battery pack when it is ready to be reconnected.

Each cell is protected from overcharging by the cell level fuel gauge and monitoring unit 2070. Diode 2030 ensures continuous cell discharging when the cell has been disconnected by the fuel gauge 2070. The unit 2070 monitors the cell status using inputs 2060. The fuel gauge and cell monitor unit 2070 is designed to monitor parameters from the Li-ion cell and report them to a controller via the data interface. Unit 2070 can be a chip such as a bq27742 single-cell Li-ion battery fuel gauge with integrated protection, available from Texas Instruments. The bq27742 fuel gauge provides information such as remaining battery capacity (mAh), state-of-charge (%), runtime to empty (minutes), cell internal impedance, voltage (mV), current (mA), and temperature (° C.), as well as recording vital parameters throughout the lifetime of the battery. Other battery fuel gauges and protectors are known in the art as well. In various embodiments, the chip 2070 can monitor parameters such as voltage, current, temperature, charge, capacity, impedance, resistance, and other parameters relevant to the operation of the cell. When the fuel gauge detects a raised temperature, over- or under-charging, or over-current, for example, the controller may direct the cell to be independently disconnected using transistor 2040. Another option is that the host controller software will force the cell to disconnect if it identifies a situation in which cell failure is imminent.

The controller (not shown) decides whether the parameters reported from the chip 2070 constitute a failure of the cell. In some embodiments, when a parameter fails to meet some objective threshold, the cell is determined to have failed and is removed. For example, if the cell capacity is 3000 mAh, but the chip 2070 reports 2000 mAh, then the controller may disconnect the cell. In some embodiments, there is a range of tolerance in which the cell will not be disconnected. For example, in a cell with 3000 mAh capacity, a 2200 mAh reading may require disconnecting, whereas a 2500 mAh reading may not. The controller may be programmed with an algorithm that determines based on all of the reported parameters, or a subset of the reported parameters, whether or not the cell is operating far from the ideal parameters that it should be removed. This may occur at a particular value of one or more parameters. The parameters may have particular bands in which they can safely operate without being disconnected.

In other embodiments, the threshold at which a cell is removed is measured with respect to the other cells rather than with respect to some objective standard. For example, if one cell is operating at 2500 mAh and the rest of the cells are operating at 2900 mAh (even when the ideal original value is 3000 mAh), the system may determine that the one cell that has a different capacity than the others should be disconnected. In that way, the threshold is not based on an objective predetermined standard, but rather is based on the observed function of the group of cells. The controller therefore monitors all of the cells and identifies the one that is different from the others. In some embodiments a combination of the objective and non-objective thresholds is used. In other words, a cell may be disconnected if it is functioning at significantly different levels than the other cells, or if all of the cells fall below a certain level (despite reporting the same parameters between them), this may indicate a fault that needs to be addressed. In some embodiments, the system allows for human intervention to manually override the decision to remove a cell from the pack. For example, if the system indicates a fault may occur but it is not definitive, the controller may trigger an alarm to alert a user, and the reconfiguration would not occur until the user took some action.

As discussed above, the battery pack of FIG. 12 is designed to reconfigure itself when one or more cells fails, as determined by the parameters sensed by the fuel gauge and cell monitor 2070. Unit 2070 can be a BMS similar to that which has been described above, acting as a sensor to receive voltage, temperature, resistance, capacitance, current, charge state, charge and discharge speed, electrolyte levels, corrosion levels, environmental conditions, or other information from each cell. In some embodiments the monitor 2070 includes the software that makes the determination of whether to disconnect the cell, and in other embodiments the information is sent to a remote controller that makes the determination. When one cell is disconnected (i.e., the number of LIB pack cells is reduced to N−1) the remaining cells are automatically protected from being overcharged. When the remaining operating cells are fully charged and the difference between the total voltage of the remaining operating cells and the charger's maximum charging voltage is less the one-cell maximum voltage, unit 2010 will operate as if the failed cell was reconnected. Transistor 2020 opens and over-charge of the working cells is prevented. For example, in a four-cell charger configured to charge up to 16.8 V, when all cells are connected, the full charge level of each cell is 4.2 V. The empty level is about 2.5 V per cell. Accordingly, in a regular charge cycle, the cells would charge from an empty level of about 10.0 V (four cells at 2.5 V each) up to a fully charged state of 16.8 V, wherein each cell is charged to 4.2 V. The charger stops charging at an accumulated voltage of 16.8 V, at which point all four cells are charged. In this same embodiment, if one cell fails and is disconnected, the maximum charge of the three remaining cells is 12.6 V. During charging with the standard 16.8 V charger, unit 2010 will detect a voltage of more than 4.2 V and will bypass the cell with transistor 2020 as previously described. The automatic failed cell detection bypass and recovery unit 2010 senses the voltage drop when the failed cell is taken offline and subsequently only allows the pack to charge to the full charge level (16.8 V) minus the maximum charge of one cell (4.2 V), for a maximum of 12.6 V. Thus, starting from the new empty cell voltage of 7.5 V (i.e., three cells at 2.5 V each), the circuit 2010 allows the pack to charge up until 12.6 V before stopping. The result is an over-charge protection system for the reduced battery pack using a standard full battery pack charger.

When a cell is disconnected as described above (i.e., the LIB pack cells count=N−1) the overcharge protection mechanism will automatically prevent the remaining cells from being over-charged. When the total voltage of the operating cells (i.e., N−1) is less than the charger voltage limits (i.e., the full charge of the standard full battery pack) unit 2010 will act as if the failed cell was reconnected, the transistor 2020 opens, and overcharge of the working cells is prevented. The overcharge protection mechanism allows the system to use a standard full pack charger on a reduced-cell battery pack.

FIG. 15 provides the detail of the unit 2010 logic that determines when to open and close transistor 2020. The auto failed cell detection bypass and recovery unit 2010 includes self-powering circuitry, which allows unit 2010 to operate while the cell has been shorted. A capacitor 4020 stores a minimal amount of energy which can be supplied to periodically open and close the transistor 2020. Unit 2010 contains resistors 4050 and 4060, diodes 4030 and 4040, a DC-DC converter 4000, and a comparator 4010. The circuitry of the unit 2010 allows the cell to be recovered even after it has been shut off from the battery power. Normally, when the cell is connected and is charging, converter 4000 and comparator 4010 receive power due to the current flowing from the high voltage to the low voltage in the battery. However, when transistor 2020 is shunted, there is no voltage drop and therefore no current going through box 2010. In order to open and close transistor 2020 to determine if the cell has been reconnected by the fuel gauge, unit 2010 needs power. To solve this problem, unit 2010 includes a built-in power source. Specifically, when the cell is disconnected, the converter and comparator are powered by a capacitor 4020, which stores energy to power the electronics inside unit 2010. When a cell has been removed, as described above, during the charging phase, capacitor 4020 receives a charge because of the voltage difference between Cell '+' and Cell '−'. When shorted, there is no voltage difference between the terminals of the cell and diode 4005 assures that current flow goes in the right direction, at which point power flows to the DC-DC converter and not back to ground. When there is a short, the circuitry of unit 2010 periodically reconnects transistor 2020 and the voltage across Cell '+' and Cell '−' gets higher again. Accordingly the circuitry shown in FIG. 15 is self-powered and can continue operating when the cell is bypassed to evaluate whether the cell has been reconnected.

The circuit shown in FIG. 15 acts like an oscillator, shorting the disconnected cell using the switch control signal, and after a period of time it opens the short in order to determine if the cell has been reconnected. If the cell fails or is disconnected or overcharged, the voltage across cell '+' and cell '−' will be greater than 4.2 V, and the oscillator will start running. It will then stop charging by opening the short for a period of time (on the order of milliseconds) to detect whether the cell has been reconnected, and if not, it will re-short the cell output for a time to allow the other cells to charge. If the cell recovers, or reconnects at any time, the oscillator will stop working, and the cell will return to its normal operation mode. Capacitor 4020 provides energy to the oscillator circuit whenever transistor 2020 shorts the battery terminals. During a short, the voltage of capacitor 4020 will drop. The short period is set such that the voltage drop will not cause comparator 4010 to stop working. Capacitor 4090 and resistor 4060 set the time that the cell is on, and resistor 4050 sets the time that the short of the failed cell is open.

Different types of capacitors that are known in the art are compatible with the disclosed system. Some capacitors provide higher density, greater storage, or other benefits. Supercapacitors or ultracapacitors, for example, are high-capacity capacitors with higher capacitance and lower voltage limits than other capacitors. They can have up to 100 times more energy per unit volume or mass than electrolytic capacitors, can accept and deliver charge much faster than batteries, and can tolerate many more charge and discharge cycles than rechargeable batteries.

The invention claimed is:

1. A system for alerting a patient, the system comprising:
 a ventricular assist device (VAD) configured to be implanted within the patient;
 a battery configured to be implanted within the patient and for providing power to at least the implanted VAD; and
 an alarm system configured to be implanted within the patient and to provide an alert to and from within the patient based on a condition.

2. The system of claim 1 wherein the alarm system is configured to provide a vibration to and from within the patient.

3. The system of claim 1 wherein the alarm system is configured to provide an electrical shock to and from within the patient.

4. The system of claim 1 wherein the alarm system is configured to provide the alert based on the implanted battery being below a threshold.

5. The system of claim 1 wherein the alarm system is configured to provide the alert based on a failure of the implanted battery.

6. The system of claim 1 wherein the alarm system is configured to provide the alert based on an error of the implanted VAD.

7. The system of claim 1 wherein the alarm system is configured to provide the alert based on an error of the implanted battery.

* * * * *